US008600513B2

(12) United States Patent
Aur et al.

(10) Patent No.: US 8,600,513 B2
(45) Date of Patent: Dec. 3, 2013

(54) SEIZURE PREDICTION AND NEUROLOGICAL DISORDER TREATMENT

(75) Inventors: Dorian Aur, Mountain View, CA (US); Izumi Toyoda, Palo Alto, CA (US); Mark R Bower, Rochester, MN (US); Paul Buckmaster, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/374,047

(22) Filed: Dec. 7, 2011

(65) Prior Publication Data
US 2012/0150257 A1 Jun. 14, 2012

Related U.S. Application Data

(60) Provisional application No. 61/459,240, filed on Dec. 9, 2010.

(51) Int. Cl.
*A61N 1/36* (2006.01)

(52) U.S. Cl.
USPC .......................................................... 607/45

(58) Field of Classification Search
None
See application file for complete search history.

(56) References Cited

U.S. PATENT DOCUMENTS

| | | | |
|---|---|---|---|
| 6,161,045 A | | 12/2000 | Fischell et al. |
| 6,658,287 B1* | | 12/2003 | Litt et al. .................. 600/544 |
| 2005/0283203 A1* | | 12/2005 | Flaherty et al. ............. 607/48 |
| 2006/0149337 A1* | | 7/2006 | John ........................... 607/45 |
| 2006/0217780 A1* | | 9/2006 | Gliner et al. ................ 607/45 |
| 2007/0213783 A1* | | 9/2007 | Pless .......................... 607/42 |
| 2007/0225674 A1* | | 9/2007 | Molnar et al. ............. 604/503 |
| 2009/0178935 A1* | | 7/2009 | Reymond et al. ........ 205/777.5 |
| 2009/0299156 A1* | | 12/2009 | Simpson et al. ........... 600/301 |

OTHER PUBLICATIONS

Torres et al. 2001, Automatic Detection of Slight Changes in NonLinear Dynamical Systems using Multiresolution Entropy Tools. International Journal of Bifurcation and Chaos (IJBC). vol. 11, Issue: 4(2001) pp. 967-981. (1 page Abstract).
Uhlhaas et al. Neural Synchrony in Brain Disorders: Relevance for Cognitive Dysfunctions and Pathophysiology. Neuron 52, 155-168, Oct. 5, 2006.
Aur et al. Understanding the physical mechanism of transition to epileptic seizures. Journal of Neuroscience Methods 200 (2011) 80-85.

(Continued)

*Primary Examiner* — Brian T Gedeon
*Assistant Examiner* — Ankit Tejani
(74) *Attorney, Agent, or Firm* — Lumen Patent Firm (57) ABSTRACT

A prediction and stimulation system or method is provided for neurological disorders characterized by a local dysfunction in neuronal activity regulation. An array of electrodes detects neuronal electrical activity of selected brain region. A detection module detects in each electrode changes in electric field and neuronal activity. A prediction module predicts for each electrode abnormal regimes determined by neurological disorder. A neuromodulation module interfaced with the electrodes selects one or more electrodes in the array where a predefined threshold has been exceeded and stimulates the brain region through each of these selected electrodes using an intermittent therapeutic stimulation pattern with a frequency between 150 and 200 Hz. The provided therapy allows for seizure prediction and detection with high accuracy, potential low risk and increased battery life. The flexibility of the method and system allows it to be used in different neurological disorders by tuning the parameters using a calibration procedure.

6 Claims, 7 Drawing Sheets

(56) References Cited

OTHER PUBLICATIONS

Aur et al. Why are seizures difficult to predict? 40th Annual Meeting of the Society-for-Neuroscience, San Diego, CA, USA Date: Nov. 13-17, 2010 vol. 40, 4 pages.
Bragin et al. High-frequency oscillations in epileptic brain. Current Opinion in Neurology 2010, 23:151-156.
Bragin et al. High-Frequency Oscillations in Human Brain. HIPPOCAMPUS 9:137-142 (1999).
Brown. Oscillatory Nature of Human Basal Ganglia Activity: Relationship to the Pathophysiology of Parkinson's Disease. Movement Disorders vol. 18, No. 4, 2003, pp. 357-363.
Crepon et al. Mapping interictal oscillations greater than 200 Hz recorded with intracranial macroelectrodes in human epilepsy. Brain 2010: 133; 33-45.
Dauwels et al. Diagnosis of Alzheimer's Disease from EEG Signals: Where Are We Standing? Current Alzheimer Research, 2010, 7, 487-505.
Jeong. EEG dynamics in patients with Alzheimer's disease. Clinical Neurophysiology 115 (2004) 1490-1505.
Pincus et al. A Regularitystatisticfor Medical Dataanalysis. Journal of Clinical Monitoring vol. 7 No. 4 Oct. 1991, pp. 335-345.
Seeck et al. Non-invasive epileptic focus localization using EEG-triggered functional MRI and electromagnetic tomography. Electroencephalography and clinical Neurophysiology 106 (1998) 508-512.
Spencer et al. Clinical Applications: MRI, SPECT, and PET. Magnetic Resonance Imaging, 1995, vol. 13; No. 8, pp. 1119-1124.
Stam. Nonlinear dynamical analysis of EEG and MEG: Review of an emerging field. Clinical Neurophysiology 116 (2005) 2266-2301.

* cited by examiner

SEIZURE PREDICTION AND NEUROLOGICAL DISORDER TREATMENT

CROSS-REFERENCE TO RELATED APPLICATIONS

This application claims priority from U.S. Provisional Patent Application 61/459,240 filed Dec. 9, 2010, which is incorporated herein by reference.

FIELD OF THE INVENTION

The invention relates to prediction and control methods and systems to treat neurological disorders. In particular, the invention relates to epileptic seizure prediction and treatment methods and systems.

BACKGROUND OF THE INVENTION

Epilepsy is a multifaceted neurological disorder where the occurrence of seizures leads to alterations in normal electric rhythms that can be recorded and analyzed. Current models show that several factors which govern neuronal excitability and intrinsic neurochemistry are involved in seizure generation, however, little is yet known about how these factors operate and determine the seizure onset. Distinct electrophysiological phenomena originating from different epileptic brain regions precede the ictal discharge.

The presence of interictal spikes has been associated with an increased risk for spontaneous seizure. In addition, during interictal periods in epileptic focal regions quasi-localized clusters of high-frequency oscillations (HFOs) have been revealed based on EEG analysis (Bragin et al., 2009; Bragin et al., 2010; Crepon et al., 2010). These HFOs appear periodically in the epileptic brain and they manifest on a scale of centimeters generated by abnormal hyper-synchronization of large neuronal ensembles. The presence of HFOs in the seizure-generating structures is highly related to temporal and spatial location of seizure onset. On the other hand few analyses have highlighted the presence of focal low frequency oscillations that precede ictal discharge in EEG or MEG data. While alterations at different levels can always facilitate abnormal neuronal activities, the occurrence of seizures is a rare event with a very low probability of occurrence.

From gene to gliogenesis and neurotransmitter release to neurogenesis all mechanisms are highly regulated in the brain. This regulation further extends to synaptic activity and firing activity of neurons in different brain regions. Therefore, changes in regulation at different levels can have broad consequences and influence rhythmic patterns of neuronal activity. The electric field generated by a population of neurons that fire action potentials was termed endogenous electric field. Changes in endogenous electric field alter the dynamics of electric charges, the diffusion of ions as well as the neurotransmitter release. All these changes can significantly influence local neuronal activity. It is the objective of the present invention to provide a method and a system using information pertaining at least some of these changes for seizure prediction and treatment of epileptic disorders as well as treatment of other neurological disorders characterized by dysfunctional regulation of neuronal activity.

SUMMARY OF THE INVENTION

The present invention provides a prediction and stimulation system or method for a neurological disorder such as an epileptic seizure disorder, Parkinson disease, Alzheimer disease, bipolar disorder, or depression. Examples of such a system or method include one or more of following structural components or method steps. An array of electrodes (preferably implanted in the brain) is used for detecting neuronal electrical activity of a brain region. A detection module interfaced with the array of electrodes is operable to detect in each of the electrodes changes in neuronal electrical activity. A prediction module predicts for each of the electrodes in the array a future occurrence of a neurological dysfunction based on the detected changes. The future occurrence of the neurological disorder is predicted when the prediction module computes that one or more parameters from the detected changes in the neuronal electrical activity exceeds a predefined threshold (e.g. determined in a calibration phase). A neuromodulation module is interfaced with the array of electrodes for selecting one or more electrodes in the array where the predefined threshold has been exceeded and stimulates the brain region through each of the selected electrodes using an intermittent therapeutic stimulation pattern with a frequency between 150 and 200 Hz. The therapeutic stimulation can be amplitude and duration modulated. In one example, one could predict or detect seizures using a low frequency oscillation with a bandwidth in the range of 0.01-1 Hz or a high frequency oscillation with a bandwidth in the range of 200-300 Hz. At least part of the detection module, prediction module and/or neuromodulation module could be manifested as an electronic unit or chip, a computer (implemented) program executable on a computer, or the like.

The present invention has at least some of the following advantages compared to current techniques. The provided therapy is an elegant solution of regulation for common neurological disorders characterized by dysfunction in neuronal regulation (e.g. epilepsy, bipolar disorders, Alzheimer disease, Parkinson, or the like). The flexibility in the method and system allows it to be used in different neurological disorders by tuning the parameters using the basic calibration as described herein. The stimulation approach of the provided therapy is efficient due to its discontinuous nature increasing the autonomy and lifetime of battery. With respect to epilepsy, the provided therapy allows for seizure prediction and detection with high accuracy. The provided treatment for seizures has a low potential risk since the amplitude of stimulation is reduced compared current prior techniques on the market. Furthermore, the provided treatment for seizures provides a therapeutics in resistant epilepsy where current drugs are inefficient.

BRIEF DESCRIPTION OF THE DRAWINGS

FIG. 5 shows according to an exemplary embodiment of the invention specific transitory behavior preceding the seizure onset and reveals a severe dysfunction in local neuronal activity regulation. The normalized change of firing rate 510 and the measure of complexity 520 is scaled and represented 1 hour prior to seizure onset. The changes that occur in firing rate correlate with alterations in the dynamics of electric charges. High values of complexity correspond to increased chaotic dynamics, which is equivalent with a significant increased disorder of the dynamic system (530 indicated regions). Each vertical arrow represents the moment when chaos (disorder) is locally generated.

FIG. 6 shows according to an exemplary embodiment of the invention details of chaos persistence represented by the area 540 in FIG. 5. Right before the seizure onset high values of complexity reveal an unusual longer period with abnormal persistent chaotic dynamics 620 that marks the transition to seizure.

DETAILED DESCRIPTION

Dysfunctional regulation of neuronal activity inside epileptogenic regions changes relevant characteristics of endogenous electric field and leads to seizure generation. A combination of features that include firing rate, power spectrum and complexity measures can be simultaneously analyzed. Preictal periods are characterized by large fluctuations of firing rate which reflect local dysfunctional regulation of neuronal activity. This local dysfunction in neuronal activity is translated in changes of endogenous electric field within clustered regions with high frequency oscillations (HFO) that act at a fundamental level of charge dynamics and lead to chaotic dynamics (high disorder) followed by electrical resonances (Crépon, et al., 2010; Bragin et al., 2010; Bragin et al., 2010; Aur and Bower, 2010, Aur, 2011). Right before the onset of seizures the presence of chaotic behavior becomes persistent and leads all types of cells to fire simultaneously and generate the transition to ictal state (Aur, 2011). At least some of the alterations in neuronal regulation involved in this transition are used as information for the seizure prediction and treatment in this invention.

As seizures originate from particular areas inside the epileptogenic regions, neuromodulation can be effective if: (i) the regions where stimulation has to be performed are detected in advance and (ii) if the therapeutic stimulation (e.g. stimulation with 150-200 Hz can be performed in a closed loop based on recorded information. Accordingly, embodiments of the invention pertain to a system and method to predict seizure occurrence and provide an effective therapeutic tool based on closed loop intermittent neurostimulation. The neurostimulation is accomplished by controlling the amplitude and the phase of the signal that provides stimulation in the preselected electrodes from an array of electrodes surgically implanted in the epileptogenic region.

Parameters required for electrical stimulation are experimentally determined during the basic calibration phase. The following are definitions of such parameters and other nomenclature used throughout this application.

HFO High Frequency Oscillations have a frequency range >200 Hz and in implementation between 200 and 300 Hz.

LFO Low Frequency Oscillations have a frequency range <1 Hz.

Chaotic Dynamics is a disordered state generated in a nonlinear dynamic system.

Persistent Chaotic Dynamics is the disordered state generated in a nonlinear dynamic system and becomes persistent if it lasts longer than 30 seconds ($T_{cr}$>0.5 min) in seizure prediction. $T_{cr}$ depends on the region where electrodes are implanted and (basic) calibration provides the value of $T_{cr}$.

Complexity Measures are measures generated to distinguish between order and disorder in a nonlinear dynamic system (some increase their values when they detect disorders e.g. Kolomogorov complexity other may decrease it). In the examples provided herein, the Kolomogorov complexity is used without limiting the invention since other complexity measures could also be used (e.g. Lyapunov exponent, algorithmic complexity measures such as Lempel-Ziv complexity, auto-mutual information, sample entropy, Tsallis entropy, approximate entropy, multiscale entropy (Li, P. Vitanyi, 2008; Dauwels et al. 2010).

Firing Rate is the number of action potentials generated during e.g. 1 second by a neuron.

Signal Complexity is measure of order (or disorder) in a recorded signal from a dynamic system (e.g EEG recordings, local field potentials in our case).

The prediction of seizures can be performed using separately any characteristics (persistent low values of mean firing rate, low values of HFO or LFO, measures of complexity, which measure the degree of disorder in dynamic recorded activity (e.g. high values of Kolmogorov complexity, persistent change in Lyapunov exponent or entropy measures) or any of their combination. Persistent in one example means that it last longer than 30 seconds ($T_{cr}$>0.5 min). Different brain regions (or patients) can have different characteristics and therefore $T_{cr}$ needs to be determined during a (basic) calibration phase. In one embodiment, the optimal parameters required to predict seizures and neuromodulation can be computed by means of a computer program executed on a computer using information from recorded or induced seizures based on low frequency stimulation (LFO). The modulation of therapeutic stimulation in time and space (electrode selection) depends on the properties of recorded local field potential.

Figure 8:
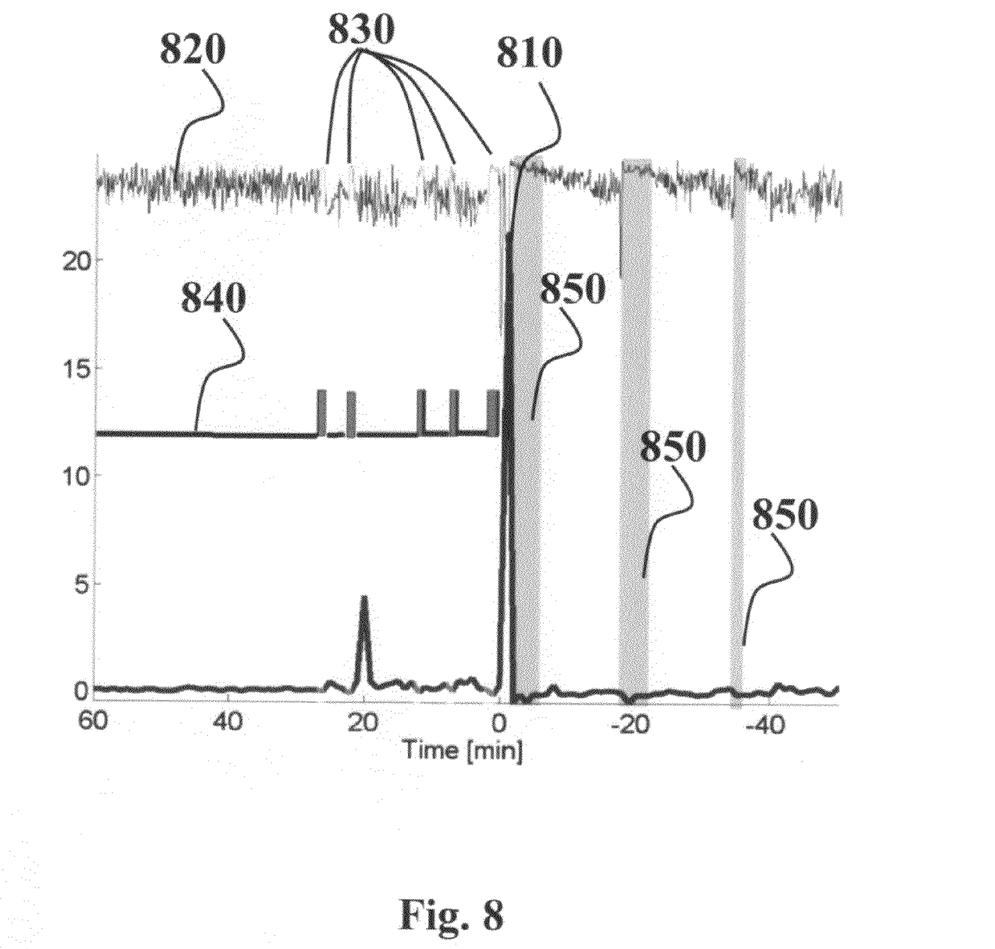
FIG. 8 shows according to an exemplary embodiment of the invention the transitory regime that precedes seizure generation (preictal state—prior to time 0) which is followed by a longer transition that occurs after the seizure (postictal phase—post time 0). The maximum of HFO amplitude 810 defines the ictal phase. The scaled changes of complexity are shown by 820. The transition during preictal period includes brief periods when chaos develops (see 830 indicated vertical lines). The therapeutic stimulation (150-200 Hz) 840 is switched on (spikes in line) and off depending on recorded activity. Longer periods of chaotic dynamics with higher values of Kolmogorov complexity (Aur and Bower, 2010; Aur 2011) develop during post-ictal phase (850). Excessive order occurs during the ictal phase and is likely to determine cognitive and motor impairment.

Implementation of embodiments of the invention require:
1. Detection of epileptogenic regions, in particular the focal regions that generate frequency oscillation using imaging techniques such as MRI, fMRI, SPECT, EEG and PET (see e.g. Seeck et al., 1998; Spencer et al., 2005).
2. An array of electrodes (e.g. FDA approved subdural strips, subdural grids or depth electrodes) that is to be surgically implanted in the epileptogenic region and well covers the active HFO regions. The number of electrodes, their configuration if possible has to be adjusted to cover the volume of epileptogenic region(s) or at least highly generating HFO areas from the epileptogenic region.
3. Record and process data from implanted electrodes from induced based on LFO stimulation (see e.g. U.S. Pat. No. 6,161,045) and non-induced, spontaneous seizures to perform basic calibration. During calibration specific required parameters for seizure prediction and neuromodulation are determined, depend on the electrode location and patient particularities. All features $T_{cr}$, $\delta_{tr}$, $\Delta_{tr}$, $A_{opt}$, $T_{opt}$ are experimentally determined during calibration:
    a. Detect changes in HFO or firing rate along with changes in signal complexity. Signal complexity is obtained by computing a measure of complexity, for example, but not limited to, Kolmogorov complexity (e.g. Li and Vitanyi, 2008).
    b. Detect the regions where (in which electrode) chaotic dynamics are persistent and predict an imminent seizure and/or stimulate the region. To prevent seizure occurrence the therapeutic stimulation (150-200 Hz) has to be provided only in the regions where persistent chaotic dynamics was detected (persistent is for example a period lasting longer than $T_{cr}$ (e.g. lasting longer than 30 s). Stimulation starts before $T_{cr}$ period, $T_s=(0.1-+=0.5)T_{cr}$ and lasts until a clear exit from chaotic dynamics is measured (See areas 530 in FIG. 5 or 830 in FIG. 8 as the start point of therapeutic stimulation—identified by spikes in line 840).

Figure 1:
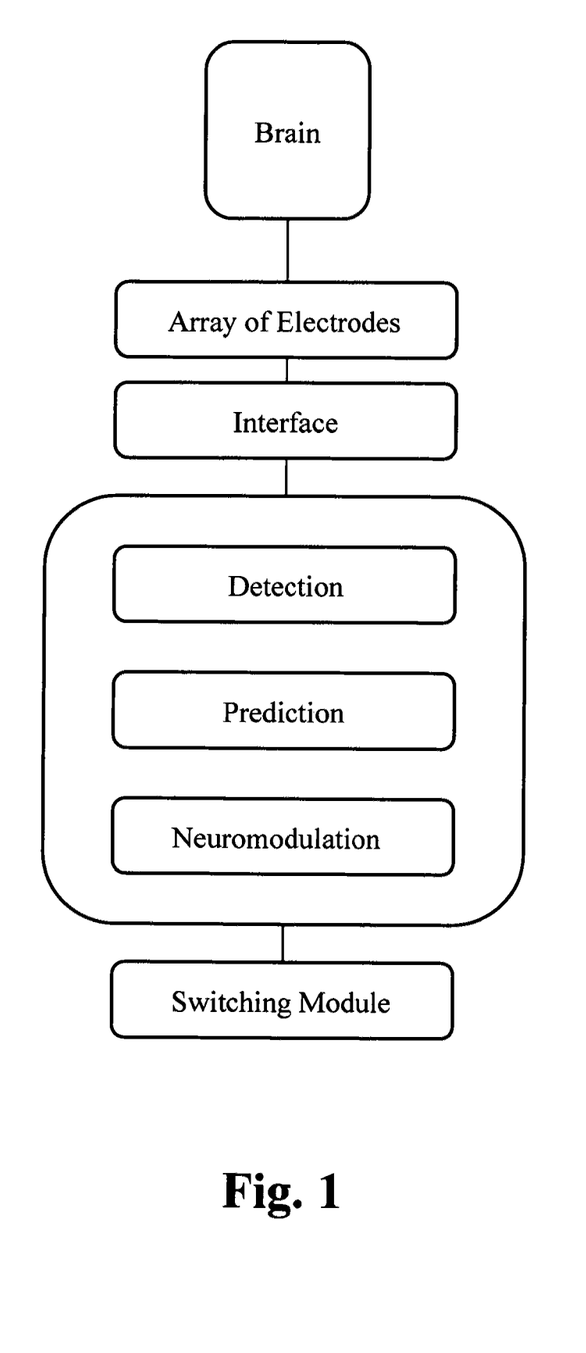
FIG. 1 shows an exemplary system for seizure prediction and neurostimulation according to an exemplary embodiment of the invention.
Figure 2:
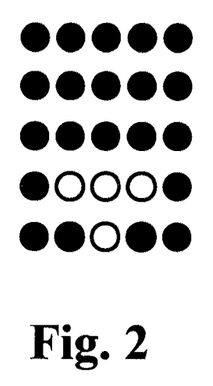
FIGS. 2-4 show three different schematic representations of changes in chaotic dynamics before seizure occurrence according to exemplary embodiments of the invention. Chaotic dynamics follows high frequency oscillation (HFO) presence in the epileptogenic region and occurs in different regions (open circles compared to the closed circles). Each circle represents an electrode in an electrode array. Effective neuromodulation targets only these specific electrodes (open circles) where the chaotic diffusion is persistent (defined as a duration larger than a (predefined) threshold).
Figure 3:
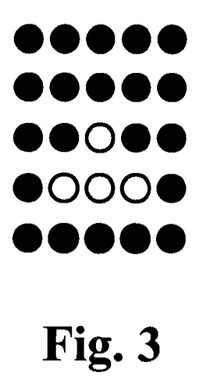
Figure 4:
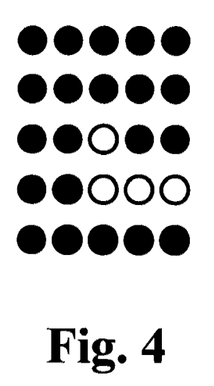

An exemplary system could include the following elements (FIG. 1):
1. Array of electrodes surgically implanted to cover the active HFO areas inside the epileptogenic region. The distance between electrodes is required to be less than 2 millimeters (preferable 400-500 micrometers) to early detect focal points with high frequency oscillations using local field potentials or changes in the firing rate. These focal points can be confirmed after electrode implants since right before the seizure every longer, persistent periods of chaotic dynamics occur which correspond to persistent low firing rate of neurons (see FIG. 6 the period 620 inside the bracket). If these periods of chaotic dynamics are shorter than 0.5 min and a seizure was generated then the electrode is not placed in the epileptogenic focal point.
2. Electronic interface composed of digital analog converters, (DAC) and analog to digital converters (ADC) filters and amplifiers required to record and provide electrical modulation.
3. Detection module where the recording signals are processed to extract the average firing rate, high frequency oscillations envelope (e.g. HFO, $200<f<300$ Hz) (Aur, 2011) and complexity measures from local field potentials in every electrode. The detection module can use different methods to estimate for every electrode in the array the average firing rate, the amplitude of HFO oscillations ($>200$ Hz) (see for example Bragin et al., 1999; Bragin et al., 2010; Crépon, et al., 2010) and the measures of complexity (see for example Pezard et al., 1997; Pincus et al., 1991; Torres et al., 2001; Small, 2005).
4. Seizure prediction module that uses the data processed from (3) signals if there is an imminent seizure. Using recorded signals, the prediction module detect periods $T_{cr}$ with persistent low firing rate (absence of firing-mean firing rate under the threshold $\delta_{tr}$ using estimations of averaging firing rate, HFO and complexity measures and signals an imminent seizure when the absence of firing and chaotic dynamics ($K>K_{tr}$, $K_{tr}=0.94$ in Kolmogorov or as a skilled artisian would readily appreciate can be differently defined if other measures of complexity are used such as a Lyapunov exponent) persists over a critical period $T_{cr}$.
5. Neuromodulation module selects the electrode where the therapeutic stimulation has to be applied and takes the decision of when the therapeutic stimulation has to be provided based on estimated firing rate values, HFO, and complexity measure. To select the electrode for therapeutic stimulation the detection of electrodes with persistent impaired neuronal activity, e.g. persistent chaotic dynamics $K>K_{tr}$ ($K_{tr}=0.94$), persistent low firing rate under the threshold $<\delta_{tr}$ Hz or persistent low HFO envelope $A_{HFO}<\Delta_{tr}$ is required. Every time when the persistent absence of firing, low persistent values of mean firing rate ($f<\delta_{tr}$), low persistent values of HFO envelope ($A_{HFO}<\Delta_{tr}$) and high values of complexity are detected ($K>K_{cr}$), the therapeutic stimulation (150-200 Hz) is switch on and then is switch off anytime between (see signal 840 in FIG. 8). To achieve optimal results of neuromodulation the stimulation needs to reduce the period with chaotic dynamics, restore order fast which is translated in a decrease complexity values ($K<<K_{tr}$) increase the mean firing rate ($f>>\delta_{tr}$) and an increase in the HFO envelope amplitude ($A_{HFO}>>\Delta_{tr}$).
6. External switching module for allowing communication between the seizure detection/stimulation device and the patient. This module could display the parameters (e.g. HFO envelope amplitude $A_{HFO}$, average firing rate, complexity measure(s) from selected electrodes), could signal an imminent seizure or could switch between different regimes during the basic calibration and parameter setup.
7. Every seizure can be well detected (see FIG. 8) based on changes in chaotic dynamics that suddenly drops, high values of HFO envelope and high values of firing rate. Persistent chaotic dynamics (about 2 min) with low firing rate and HFO regime precede and follows the moment of seizure generation.

Seizure Prediction Module

All recorded data processed in the detection module could be used to predict the seizure (e.g. average firing rate, HFO, complexity measure). Chaotic dynamics caused by synchronous firing is maintained in the absence of spikes or during a low firing rate in the epileptogenic region. Therefore, it is important to detect periods with persistent low firing rate (absence of firing) using estimations of averaging firing rate, HFO envelope ($A_{HFO}$) and complexity measures. The periods when the complexity measure has continuously high values or exceeds a predefined threshold correspond to persistent chaos development (See 530 in FIG. 5 or 830 in FIG. 8). Persistent chaotic dynamics over a certain critical time, $T_{cr}$ in the epileptogenic region leads to seizure generation. Therefore, detecting the maximum period of persistent chaotic dynamics $T_{cr}$ that does not generate a seizure in the epileptogenic region is important for seizure prediction. The critical time $T_{cr}$ can be obtained by finding the maximum periods of time when the values of complexity are continuously greater than a threshold (See 530 in FIG. 5 or 830 in FIG. 8) and there are no seizures that follows these periods. In addition local regulatory disfunction persistent chaotic dynamics followed by abnormal simultaneous firing (synchrony) can lead to cognitive impairments in bipolar disorders or Alzheimer's disease and in basal ganglia leads to Parkinsonian tremor.

An example of implementation requires:
Step 1: Estimate the critical time $T_{cr}$ as the maximum period when the firing rate f and/or the envelope of HFO have persistently low values ($f<\delta_{tr}$, ($A_{HFO}<\Delta_{tr}$) and/or chaotic dynamics is continuously (e.g., but not limited to K>0.94) present in the epileptogenic region and does not generate a seizure.
Step 2: Detect the absence of firing and chaotic dynamics which persists over $T_{cr}$ ($T>T_{cr}$) and signal an imminent seizure or provide therapeutic stimulation in advance (see example in FIG. 9). The beginning of stimulation should precede $T_{cr}$ (Ts=(0.1-0.5)$T_{cr}$).

Figure 5:
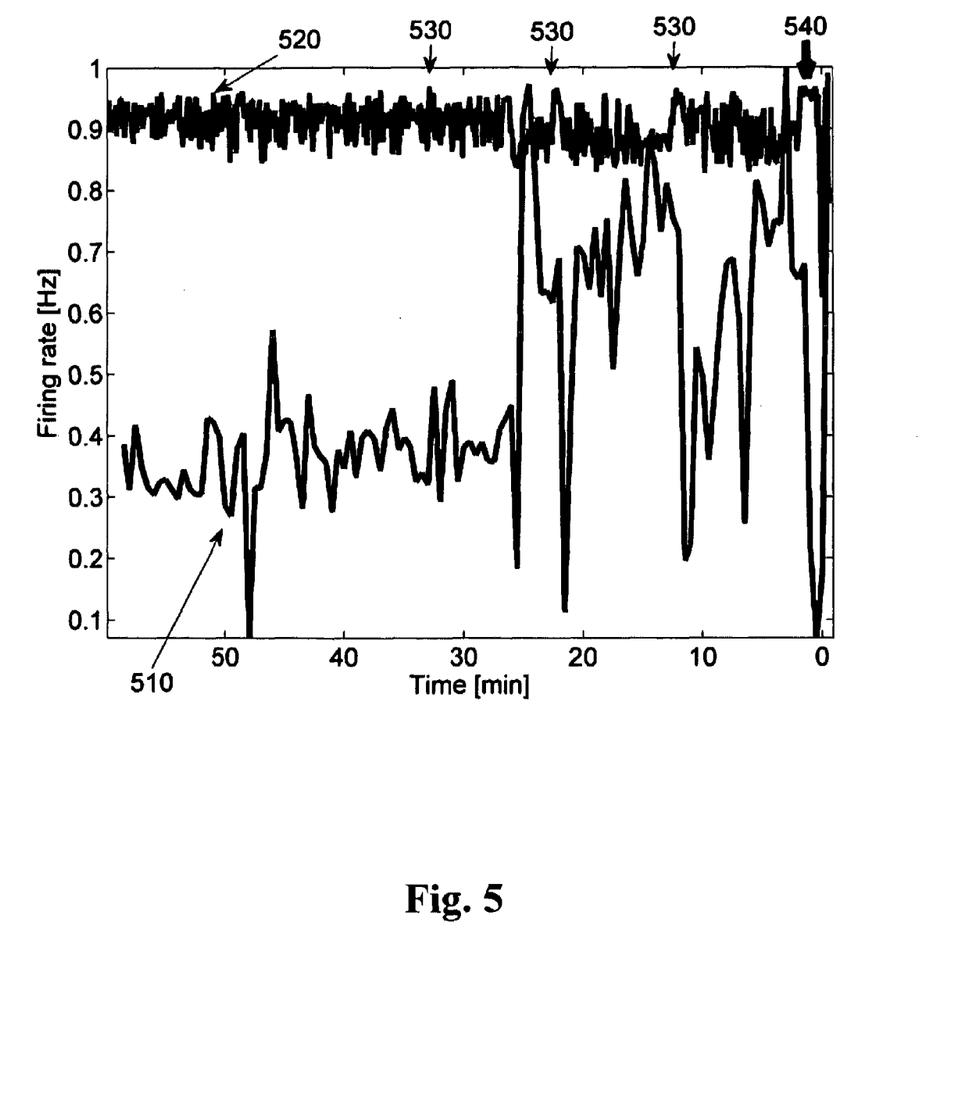

In the example of FIG. 5, high values of complexity (K>$K_{tr}$) correspond to an increased chaotic dynamics (See 530 in FIG. 5 or 830 in FIG. 8, FIG. 9) which are periods when chaotic dynamics becomes persistent. This information is translated in FIG. 7. Each vertical line represents the duration of persistent chaotic dynamics, which is less than 0.5 min represented by the dashed bar ($T_{cr}$=0.5 min). It is likely that $T_{cr}$ depends on particular characteristics of epileptogenic regions and networks involved in seizure generation.

Figure 7:
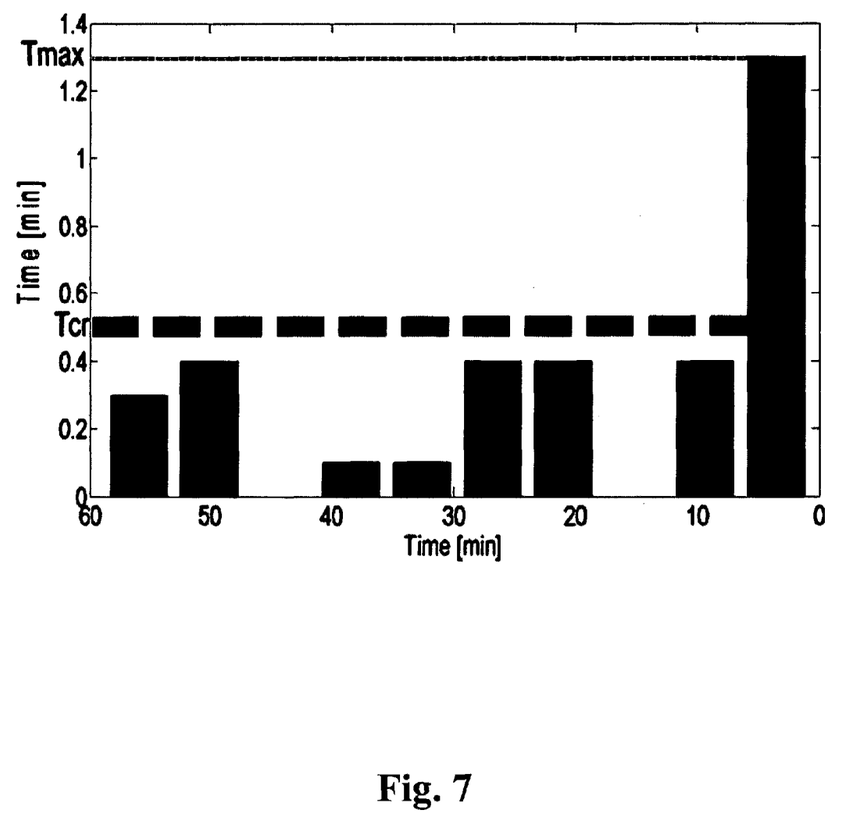
FIG. 7 shows according to an exemplary embodiment of the invention the presence of persistent chaotic dynamics represented 1 hour before the onset of a seizure. Right before the seizure onset unusual persistent chaotic dynamics is detected which reflects local increased disorder in the dynamics of recorded signal. Each vertical line represents the duration when chaos (disorder) is locally generated. The enhanced arrow points to the period when chaotic dynamics persists longer than 0.5 min (about 2 min). The horizontal dashed line marks the critical time ($T_{cr}\sim=0.5$ min). The seizure is a rare event that occurs only if chaotic dynamic lasts longer than $T_{cr}$.

For each generated seizure the prediction horizon $T_h$ can be computed as the difference between the period of time when chaotic diffusion is detected right before the seizure ($T_{max}$) and the critical time $T_{cr}$:

$$T_h = T_{max} - T_{cr} \quad (1)$$

where $T_{max}$ is the period of continuous persistent chaotic dynamics that precedes the seizure. In many cases the nonlinear behavior of the system limits this horizon of prediction to less than one minute. In case of (FIG. 7) the prediction horizon is $T_h$=0.7 min ($T_{max}$=1.2 min and $T_{cr}$=0.5).

Neuromodulation Module: The Close Loop Therapeutic Stimulation

The neuromodulation module contains an electric source that can generate therapeutic stimulation in a selected bandwidth (150-200 Hz) with controllable amplitude. Since the decrease in firing activity within the epileptogenic region is related to persistent chaotic diffusion then the therapeutic stimulation only in the regions where chaotic dynamics was detected has positive effects, increases the firing rate and reduces the incidence of spontaneous spikes and seizures. To achieve optimal results the stimulation has to be discontinuously applied only when and where chaotic dynamics is persistently detected in the epileptogenic HFO regions, basically following the amplitude and the phase of complexity measure represented by markers 530 in FIG. 5 or 830 in FIG. 8.

Figure 9:
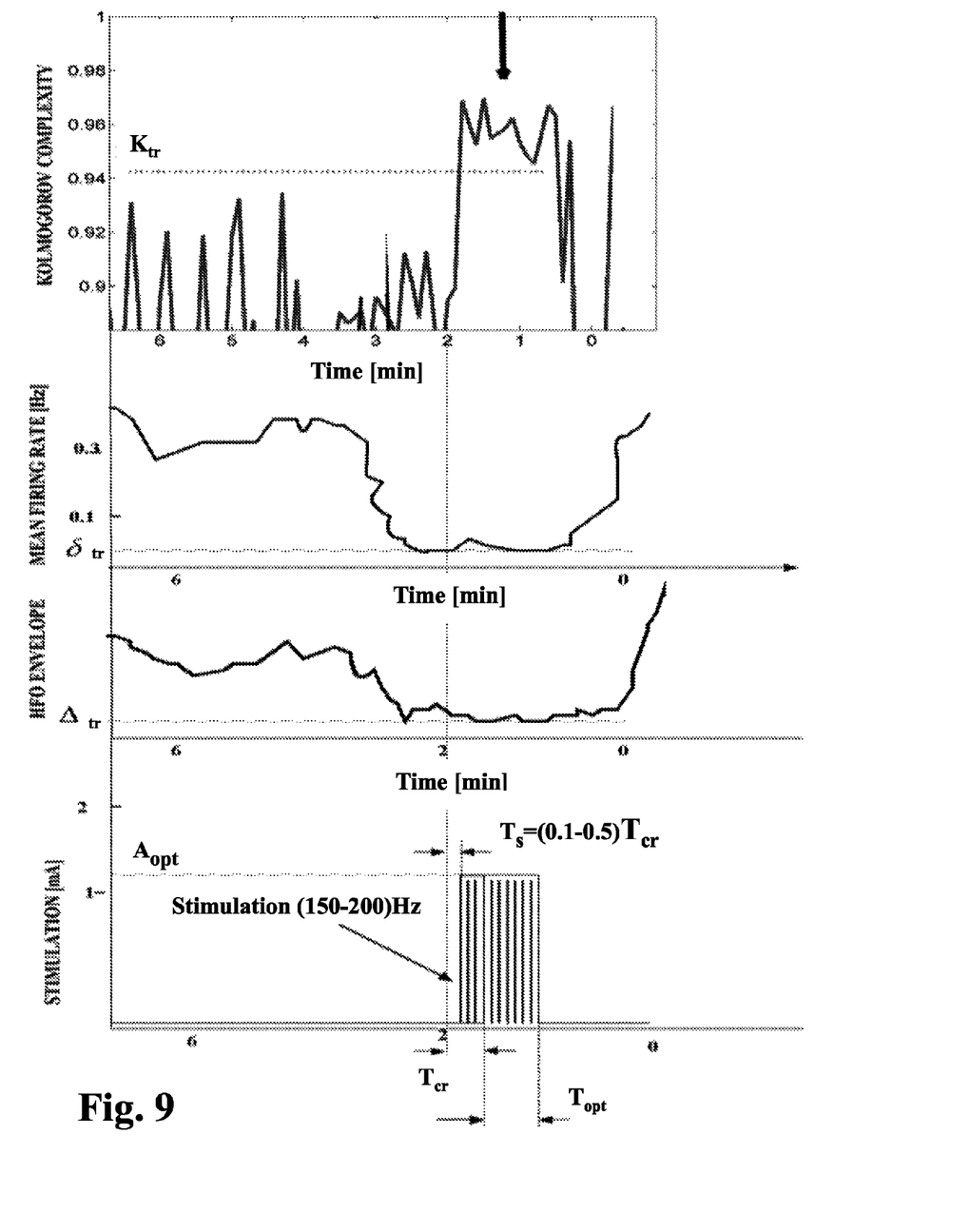
FIG. 9 shows according to an exemplary embodiment the therapeutic stimulation with 150-200 Hz is applied before $T_{cr}$ which is until the firing rate and HFO envelope reach significant levels over the threshold measures ($\delta_{tr}$, $\Delta_{tr}$). The optimal amplitude of stimulation $A_{opt}$ depends on local characteristics where the electrodes are implanted. The arrow in FIG. 9 shows the period with increased chaotic dynamics ($K>K_{tr}$) which is the same period indicated by 620 or 540.

There are several steps that have to be followed to provide efficient neuromodulation:
1. Identify the electrodes where persistent chaotic dynamics occurs and start the stimulation when $T_s$=(0.1-0.5) $T_{cr}$. It is noted that this relationship can be applied in all neurological disorder where persistent chaotic dynamics is a result of dysfunctional regulation of neuronal activity.
2. Control the phase of therapeutic stimulation (150-200 Hz) to follow periods 530 in FIG. 5 or 830 in FIG. 8 when higher chaotic dynamics is detected by the complexity measure. Additionally, measures of firing rate or HFO amplitude of harmonics can be used to additionally control the phase. A threshold that indicates when a sudden decrease of firing rate (decrease in HFO amplitude) is associated with an increase in signal complexity provides the beginning of therapeutic stimulation stimulation (FIG. 9).

One exemplary embodiment of implementation requires:
a. Step 1: Detect the electrodes where there is a persistent absence of neuronal activity (low values of mean firing rate <$\delta_{tr}$, low values of HFO envelope (200<f<300 Hz)<$\Delta_{tr}$, high values of complexity >Ktr).
b. Step 2: In these detected electrodes, if $T_s$>(0.1-0.5)$T_{cr}$ switch on the therapeutic stimulation (150-200 Hz) when low values of mean firing rate, and/or low values of HFO envelope and/or high values of complexity are detected and switch off anytime between (see 840 in FIG. 8). The $T_{cr}$ value represents how long the absence of firing and chaotic dynamics persist in the epileptic region without generating a seizure.

To provide optimal values for neuromodulation the threshold value has to be determined along with other parameters of stimulation following the procedure described in basic calibration.

In some examples of the invention drug therapy can be added effectively to the methods describes herein if it jointly attacks the dynamics of seizure generation.

Flexibility of the system can be achieved by switching between three different regimes:

Basic Calibration Phase:

Since slight difference in network property depend on specific electrophysiological properties of epileptogenic region then the optimal values for neuromodulation are particular to a selected specific region and depend from patient to patient. Therefore, threshold values ($T_{cr}$, $\delta_{tr}$, $\Delta_{tr}$, $K_{tr}$) and optimal values of stimulation (amplitude $A_{opt}$, frequency $f_{opt}$) have to be experimentally determined. To obtain the required parameters for seizure prediction ($T_{cr}$, $\delta_{tr}$, $\Delta_{tr}$, $K_{tr}$) in the selected region a seizure has to be recorded to observe how these measures firing rate, Kolmogorov complexity, HFO envelope evolve right before seizure generation (see FIG. 9). Then these threshold values can be extracted directly from the plots, example $K_{tr}$ in FIG. 9 a, $T_{cr}$ from FIG. 7. After determining these threshold values the main strategy to find optimal values of neurostimulation is to generate a seizure providing LFO stimulation in the region and stop the generating seizure using therapeutic stimulation (see e.g. U.S. Pat. No. 6,161,045). The optimal features can be obtained by varying the parameters of stimulation within a frequency band f=150-200 Hz to increase the firing rate and reduce the duration of chaotic dynamics in the epileptogenic region. The optimal amplitude of stimulation $A_{opt}$ is determined to allow a fast optimal time ($T_{opt}$) of exit from the persistent chaotic regime that occurs before the seizure. If periods before $T_{cr}$ are well detected a lower amplitude $A_{opt}$ can reduce the tissue damage by using stimulation parameter settings of low amplitudes and short pulse widths.

Importantly, the basic calibration regime can be used to readjust all parameters required in seizure prediction or neuromodulation periodically in case of significant changes in the structure or function of neurons in the region.

Figure 6:
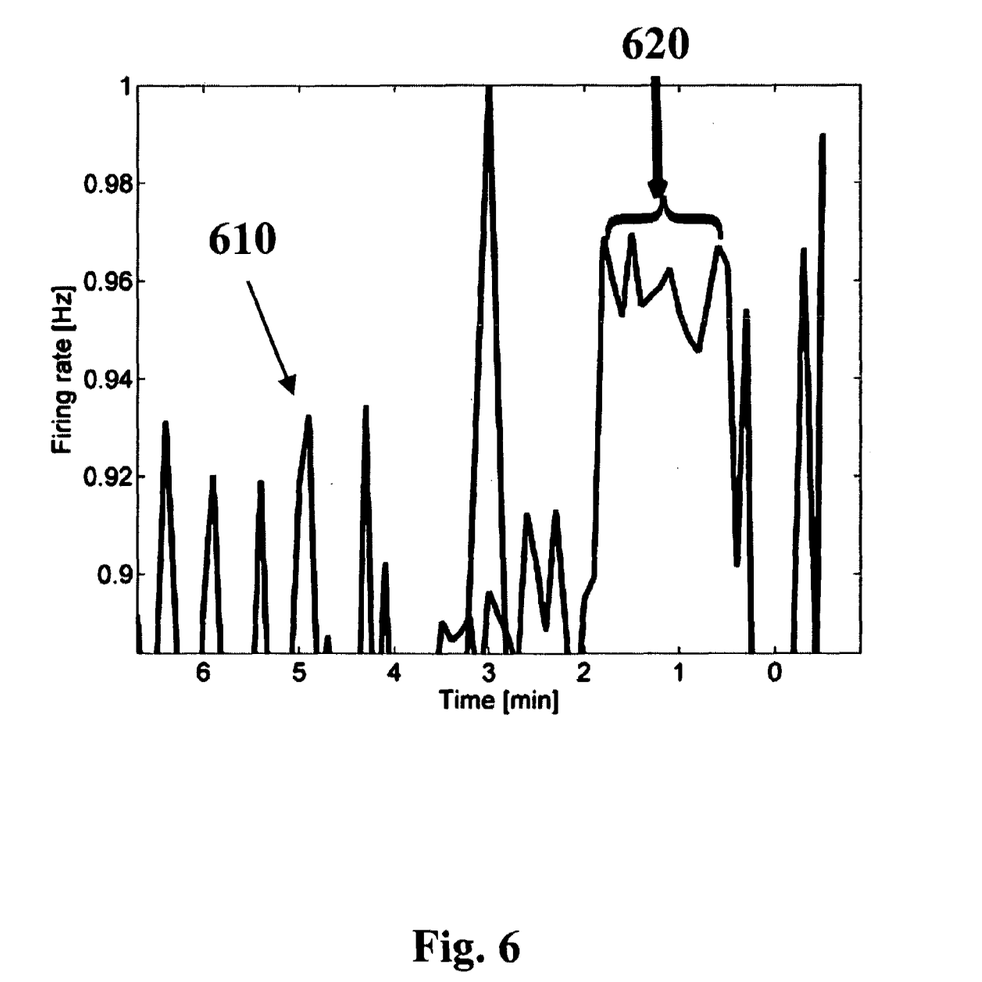

Chaotic dynamics is determined by changes in firing rate 510 in FIG. 5 and is correlated with changes in high frequency oscillations (HFO) 610, 620 in FIG. 6. To improve the robustness of early seizure prediction and neurostimulation the complexity measures can be combined with changes in the mean firing rate characteristics $f_r$ and in the amplitude of HFO envelope ($A_{HFO}$) as the estimated principal component. To reliably predict the seizure outcome a detection when these values are under a given threshold (tr) is required:

$$f_r < \delta_{tr}; A_{HFO} < \Delta_{tr}; K > K_{tr} \quad (2)$$

Where $\delta_{tr}$, $\Delta_{tr}$, $K_{tr}$ are the threshold values for the average firing rate, HFO envelope and Kolmogorov complexity determined during the basic calibration phase for every region where stimulation needs to be performed (see example in FIG. 9) and correlated with the increase in chaotic dynamics. In the example these critical values can be directly obtained from $f_r \leq 0.1$ Hz and $A_{HFO} \leq 0.05$. Therefore if chaotic diffusion is detected for a period T and $T > T_{cr}$ and $f_r < \delta_{tr}$; $A_{HFO} < \Delta_{tr}$ the device has to signal an imminent seizure. It is unlikely to obtain accurate predictions if the recordings are made far from HFO epileptogenic regions. To prevent this issue the present method requires to cover with electrodes the source of seizure, the entire epileptogenic area.

Since there is a close relation between neuronal activity, electric field and dynamics of electric charges, large fluctuations of firing rate reflect local dysfunctional regulation of neuronal activity. Periods that display persistent chaotic dynamics are followed by aberant synchrony in epilepsy (Aur, 2011), Alzheimer's Disease (Jeong, 2004; Stam, 2005; Dauwels et al., 2010) and Parkinson (Brown 2003). In addition to epilepsy many recognized neurological disorders such as schizophrenia autism, cognitive or mood disorders are associated with abnormal neural synchronization (Uhlhaas and Singer, 2006). Furthermore, the persistence of low (close to zero) abnormal firing rate associated with chaotic dynamics is a common characteristic in other neurological disorders in Parkinson, Alzheimer, bipolar disorders, depression. Therefore and even though the examples so far pertain to epileptic disorders, the closed-loop neuromodulation technique described herein can also be used in the above disorders by adjusting the critical time ($T_{cr}$) to smaller values to disrupt longer periods of chaotic dynamics. The critical time is dependent on the patient, region, type of disorder. For example, one could record local field potentials from selected region and determine all periods with increased chaotic dynamics (e.g. $K_{tr} > 0.94$) as in FIG. 7 and estimate $T_{cr}$. Then apply therapeutic stimulation to reduce periods with persistent chaotic dynamics $T_s = (0.1-0.5) T_{cr}$.

REFERENCES

Aur D. Understanding the Physical Mechanism of Transition to Epileptic Seizures, Journal of Neuroscience Methods, Volume 200, Issue 1, 30 Aug. 2011, pp 80-85.
Aur D, Bower, M. 2010 Why are Seizures Difficult to Predict? 40th Annual Meeting of the Society-for-Neuroscience, San Diego, Calif., USA Date: November 13-17, Volume: 40.
Aur D., Jog, M, 2010, Neuroelectrodynamics—Understanding The Brain Language, IOS Press http://dx.doi.org/10.3233/978-1-60750-473-3-i.
Bragin, A., Engel Jr., J., Wilson, C. L., Fried, I., Buzsáki, G. 1999 High-frequency oscillations in human brain, Hippocampus 9 (2), pp. 137-142.
Bragin, A., Engel, J., Staba, R. J. 2010, High-frequency oscillations in epileptic brain, Current Opinion in Neurology 23 (2), pp. 151-156.
Brown, P. 2003 Oscillatory nature of human basal ganglia activity: Relationship to the pathophysiology of parkinson's disease. Movement Disorders 18 (4), pp. 357-363.
Crépon, B., Navarro, V., Hasboun, D., Clemenceau, S., Martinerie, J., Baulac, M., Adam, C., Le Van Quyen, M. 2010, Mapping interictal oscillations greater than 200 Hz recorded with intracranial macroelectrodes in human epilepsy, Brain 133 (1), pp. 33-45.
Dauwels, J., Vialatte, F., Cichocki, A. 2010 Diagnosis of Alzheimer's disease from EEG signals: Where are we standing? Current Alzheimer Research 7 (6), pp. 487-505.
Jeong, J. 2004 EEG dynamics in patients with Alzheimer's disease, Clinical Neurophysiology 115 (7), pp. 1490-1505.
Pincus S. M., Gladstine I. M. and Ehrenkranz R. A., 1991, A regularity statistic for medical data analysis, J Clin Monit 7 (1991), pp. 335-345.
Seeck, M. Lazeyras, F. Michel, C. M. Blanke, O. Gericke, C. A. Ives, J. Delavelle, J. Golay, X. Haenggeli, C. A. De Tribolet, N. 1998 Non-invasive epileptic focus localization using EEG-triggered functional MRI and electromagnetic tomography, Electroencephalography And Clinical Neurophysiology, VOL 106; Number 6, pages 508-512.
Spencer, S. S. Theodore, W. H. Berkovic, S. F. Clinical Applications: MRI, SPECT, and PET, Magnetic Resonance Imaging, 1995, Vol 13; Number 8, pages 1119-1124.
Stam, C. J. 2005, Nonlinear dynamical analysis of EEG and MEG: Review of an emerging field Clinical Neurophysiology 116 (10), pp. 2266-2301.
Torres et al. 2001, Automatic Detection of Slight Changes in NonLinear Dynamical Systems using Multiresolution Entropy Tools. International Journal of Bifurcation and Chaos (IJBC). Volume: 11, Issue: 4(2001) pp. 967-981.
Uhlhaas, P. J., Singer, W. 2006, Neural Synchrony in Brain Disorders: Relevance for Cognitive Dysfunctions and Pathophysiology Neuron 52 (1), pp. 155-168.
M. Li, P. Vitanyi 2008 An Introduction to Kolmogorov Complexity and Its Applications Springer Verlag (book) pp. 101-331.

What is claimed is:

1. A prediction and closed-loop stimulation method for neurological dysfunction therapy, comprising:
  (a) detecting neuronal electrical activity of a brain region via an array of electrodes, wherein said array of electrodes is adapted to cover a region of dysfunctional neuronal activity of said brain region;
  (b) continuously detecting in each of said electrodes periods that last at least 30 seconds with (i) persistent chaotic dynamics in local field potentials, (ii) persistent values of high frequency oscillations in the range of 200-300 Hz within said local field potentials, and (iii) persistent low firing rates close to zero;
  (c) predicting for each of said electrodes in said array of electrodes a future occurrence of a neurological dysfunction, wherein said future occurrence of said neurological dysfunction is predicted when a prediction module computes that (j) said persistent chaotic dynamics exceeds a predefined threshold for said persistent chaotic dynamics for said at least 30 seconds, (jj) said persistent values of high frequency oscillations exceeds a predefined threshold for said persistent high frequency oscillations for said at least 30 seconds, (jjj) said persistent low firing rates exceed a predefined threshold defined for said persistent low firing rates for said at least 30 seconds, or (ij) any combination thereof; and
  (d) selecting using a neuromodulation module a subset of electrodes from said array of electrodes, wherein said subset of electrodes is defined as said electrodes in said array of electrodes where said future occurrence of said neurological dysfunction was predicted by said prediction module and then prior to an onset of said neurological dysfunction stimulating said brain region through said subset of electrodes selected by said neuromodulation module using an intermittent therapeutic stimulation pattern with a frequency between 150 and 200 Hz.

2. The method as set forth in claim 1, wherein said intermittent therapeutic stimulation pattern is amplitude and duration modulated.

3. The method as set forth in claim 1, wherein each of said predefined thresholds are determined by a calibration phase.

4. The method as set forth in claim 1, further comprising detecting in each of said electrodes persistent values of low frequency oscillations in the range of 0.01-1 Hz within said local field potentials, and wherein said future occurrence of said dysfunctional neuronal activity is further predicted when said prediction module computes that said persistent values of low frequency oscillations exceeds a predefined threshold for said persistent low frequency oscillations.

5. The method as set forth in claim 1, wherein said electrodes in said array of electrodes have a distance between each other of less than 2 millimeters.

6. The method as set forth in claim 1, wherein said electrodes in said array of electrodes have a distance between each other of 400 to 500 micrometers.

* * * * *